(12) United States Patent
Li et al.

(10) Patent No.: US 7,587,279 B2
(45) Date of Patent: Sep. 8, 2009

(54) METHOD FOR QUANTITATIVE PCR DATA ANALYSIS SYSTEM (QDAS)

(75) Inventors: Xitong Li, Mountain View, CA (US); Kenneth Stineman, San Jose, CA (US)

(73) Assignee: Genomic Health, Redwood City, CA (US)

( * ) Notice: Subject to any disclaimer, the term of this patent is extended or adjusted under 35 U.S.C. 154(b) by 306 days.

(21) Appl. No.: 10/886,501

(22) Filed: Jul. 6, 2004

(65) Prior Publication Data

US 2006/0008809 A1 Jan. 12, 2006

(51) Int. Cl.
*G01N 33/48* (2006.01)
*C12P 19/34* (2006.01)

(52) U.S. Cl. ........................................ 702/17; 435/91.2

(58) Field of Classification Search ........................ None
See application file for complete search history.

(56) References Cited

U.S. PATENT DOCUMENTS 6,730,501 B2 * 5/2004 Eyre et al. .................. 435/91.2

FOREIGN PATENT DOCUMENTS

| WO | WO 99/02714 | 1/1999 |
|---|---|---|
| WO | WO 00/50595 | 8/2000 |
| WO | WO 00/55173 | 9/2000 |
| WO | WO 01/40466 | 6/2001 |
| WO | WO 01/55320 | 8/2001 |
| WO | WO 01/70979 | 9/2001 |
| WO | WO 02/00677 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/46467 | 6/2002 |
| WO | WO 02/055988 | 7/2002 |
| WO | WO 02/059377 | 8/2002 |
| WO | WO 02/068579 | 9/2002 |
| WO | WO 02/103320 | 12/2002 |
| WO | WO 03/083096 | 10/2003 |

OTHER PUBLICATIONS

"Data Analysis on the ABI Prism 7700 Sequence Detection System: Setting Baselines and Thresholds", 2002 [retrieved on Apr. 17, 2007]. Retreived from the Internet: <URL:http://www.appliedbiosystems.com/support/apptech/#rt_pcr2>.*
"Real-Time PCR Vs. Traditional RCR", 2003 [retreived on Apr. 17, 2007]. Retreived from the Internet: <URL:http://www.appliedbiosystems.com/support/apptech/#rt_pcr2>.*
Knutsson et al., "Development of a PCR-compatible enrichment medium for *Yersinia enterocolitica*: amplification precision and dynamic detection range during cultivation," International Journal of Food Microbiology, vol. 72 (2002) pp. 185-201.*
"Data analysis on the ABI prism 7700 Sequence detection system: Setting baselines and thresholds", Applied Biosystems, pp. 1-12, (2002).
"Real-Time PCR vs. Traditional RCR", Applied Biosystems, pp. 1-13, (2003).
U.S. Appl. No. 10/886,019, filed Jul. 6, 2004 entitled "Quantitative PCR Data Analysis System (QDAS)."

* cited by examiner

*Primary Examiner*—Mary K Zeman
*Assistant Examiner*—Anna Skibinsky
(74) *Attorney, Agent, or Firm*—Townsend and Townsend and Crew LLP

(57) ABSTRACT

This invention provides a method for the quantitation and quality assurance of QPCR data. In particular, the invention provides a method for extracting data curves from a QPCR assay, estimating the shape and characteristics of an amplification curve and producing a quality score metric. The invention also provides a robust method for calculating a threshold cycle ($C_T$) value and classifying the status of the QPCR results.

78 Claims, 15 Drawing Sheets

Figure 1: QPCR Assay Plotted on a Linear Scape
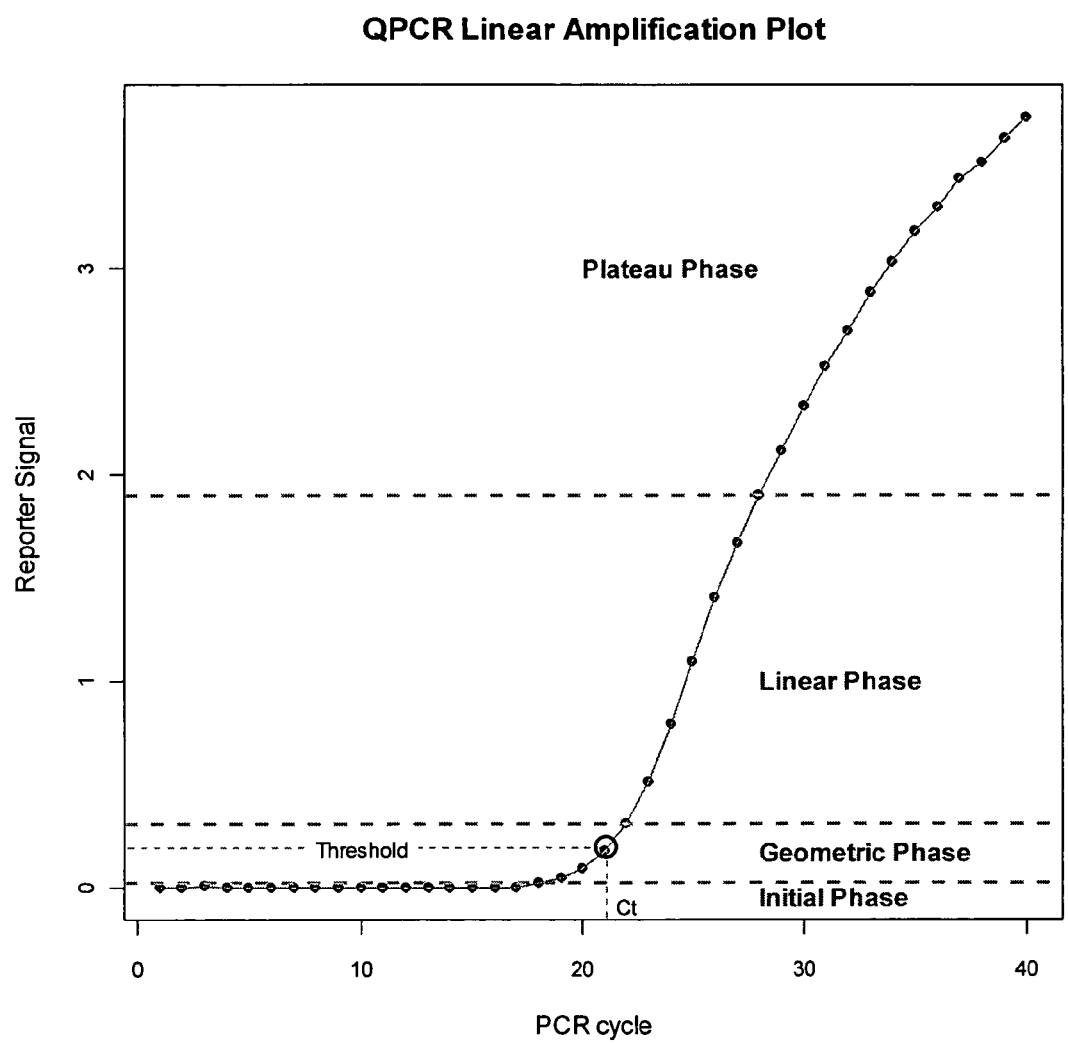

Figure 2: QPCR Assay plotted on a logarithmic scale
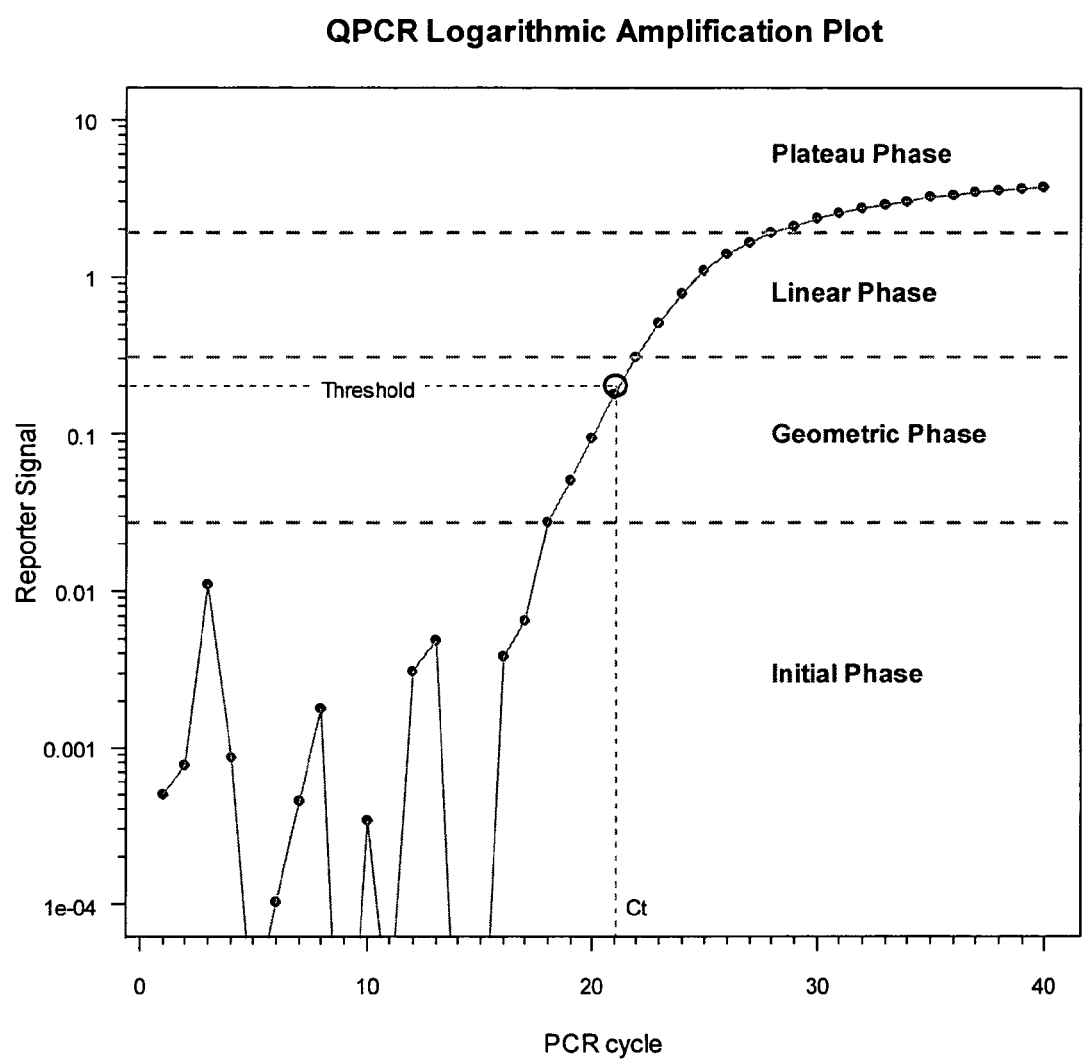

Figure 3: Threshold Window, Maximum LQV Window, and CT Computation
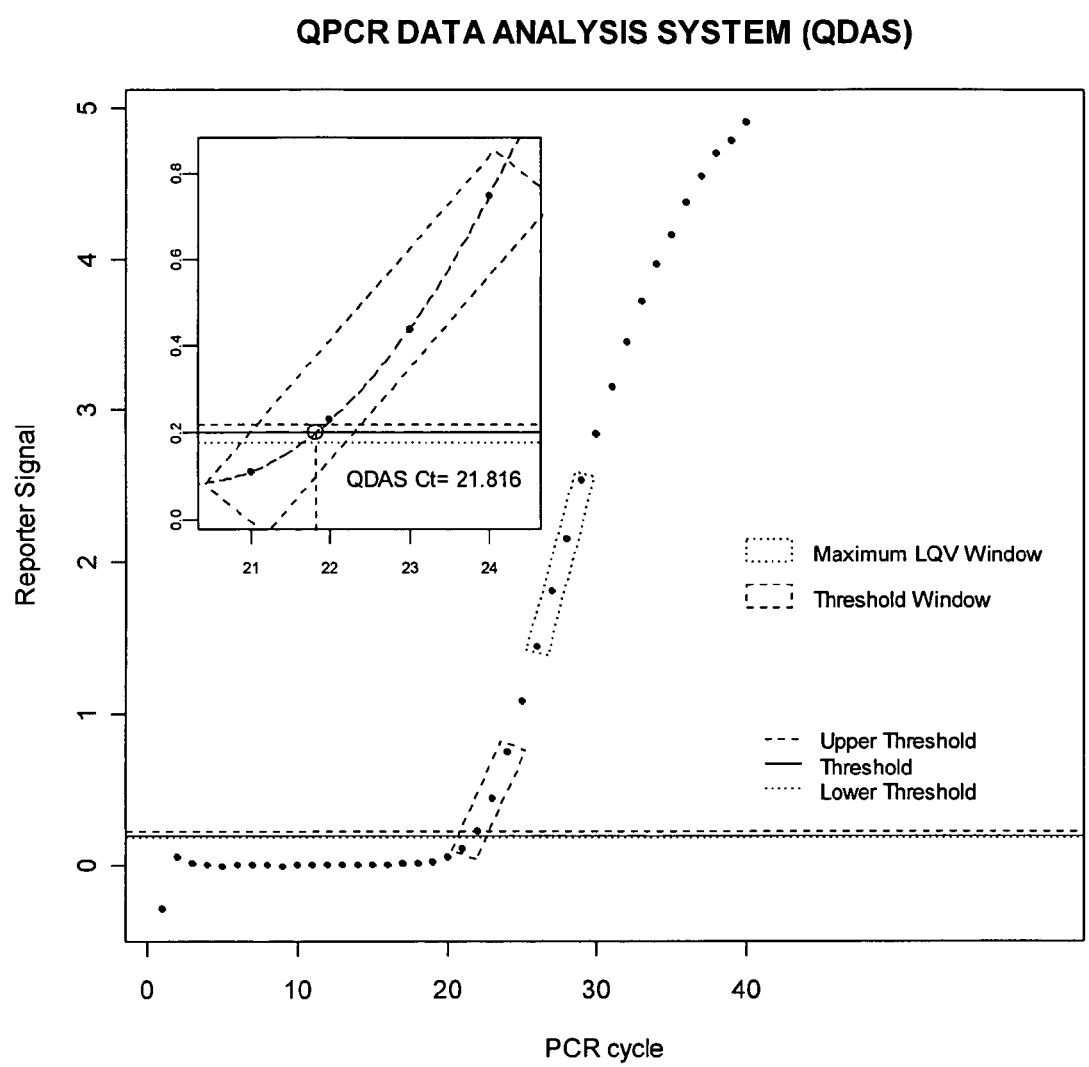

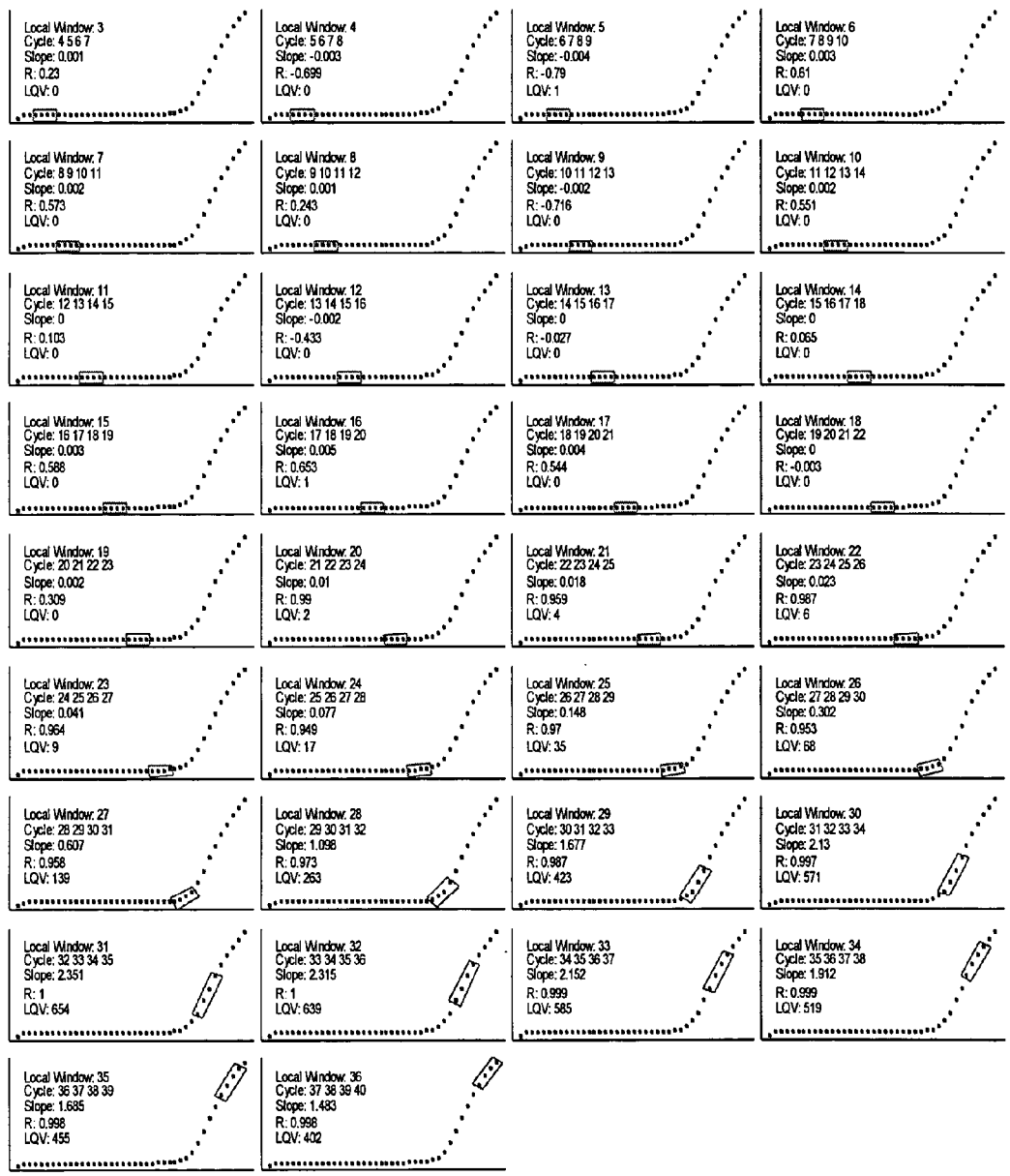
Figure 4: Windowing Method

Figure 5 Flowchart for computing Quality Score (QS) and Maximum LQV Window (MLW).
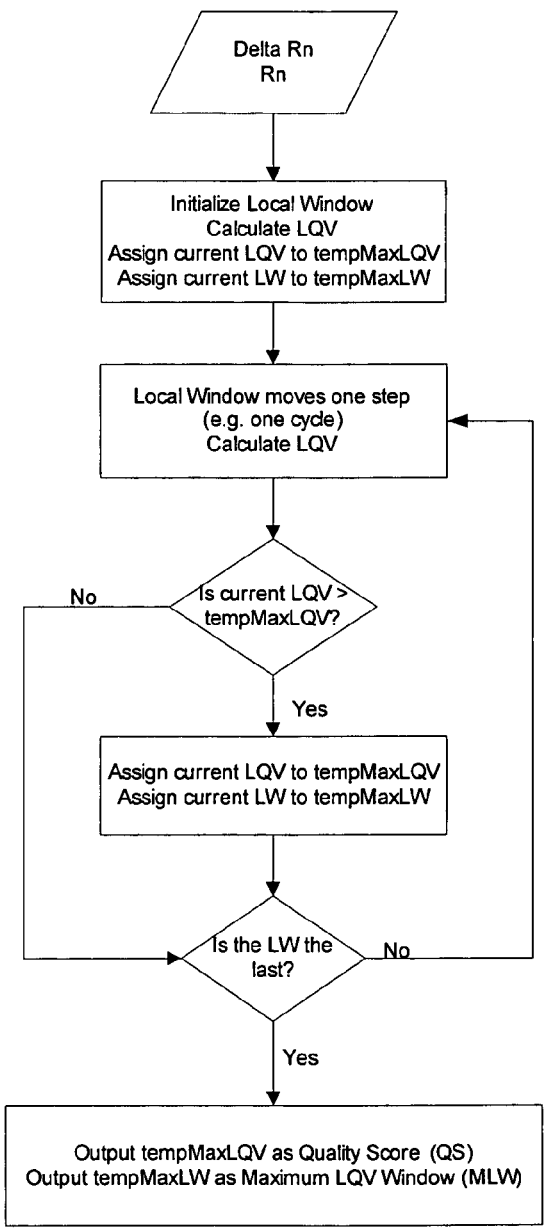

Figure 6: Flowchart for determining the QDAS Threshold Window.
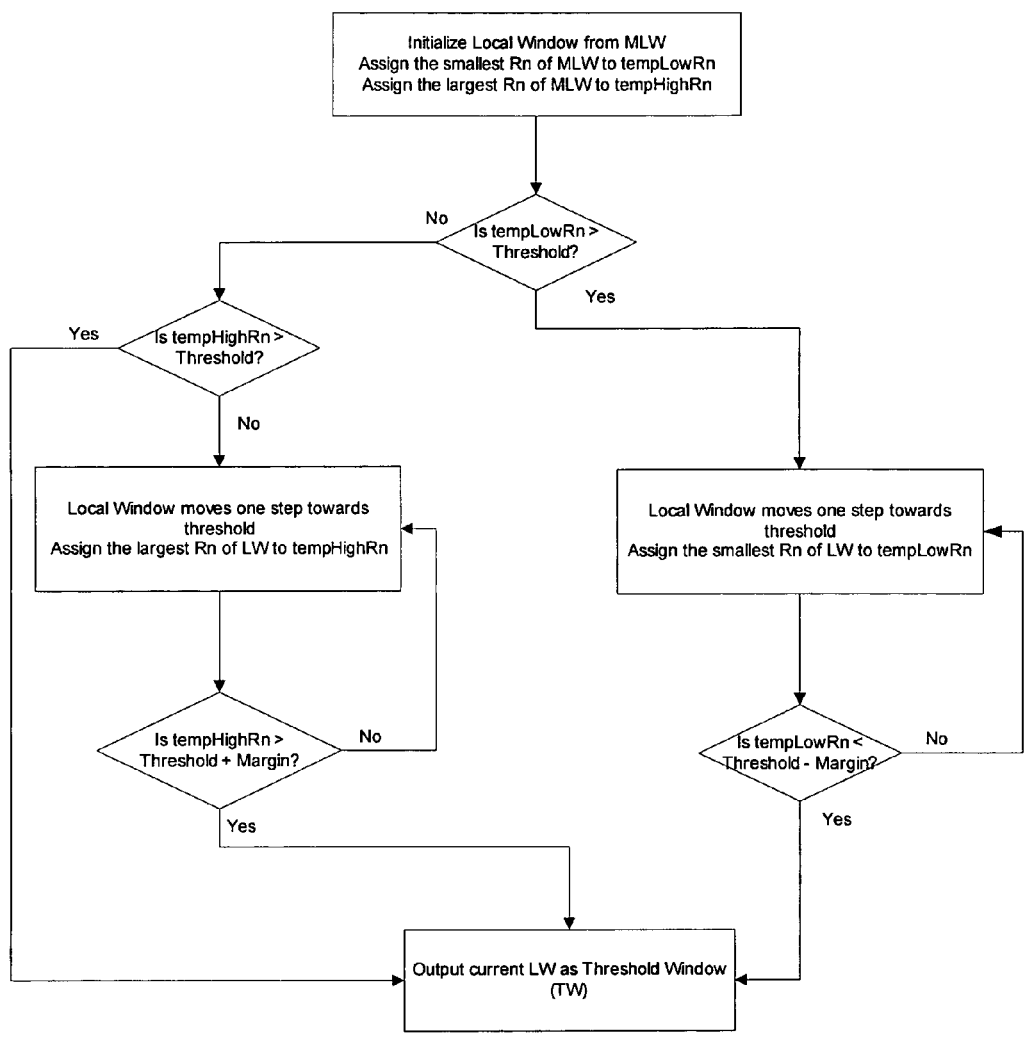

Figure 7: Background Signal distribution versus CT
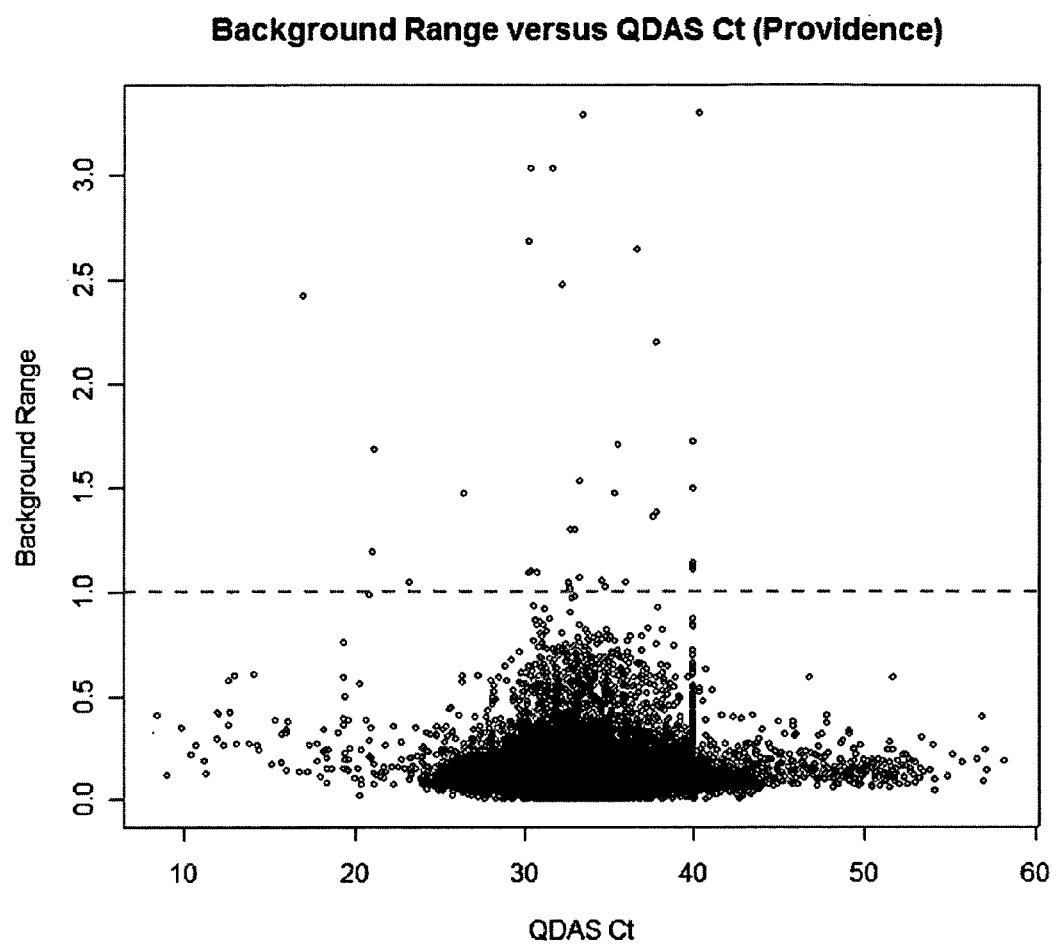

Figure 8. Quality Lower Limit Function based classification
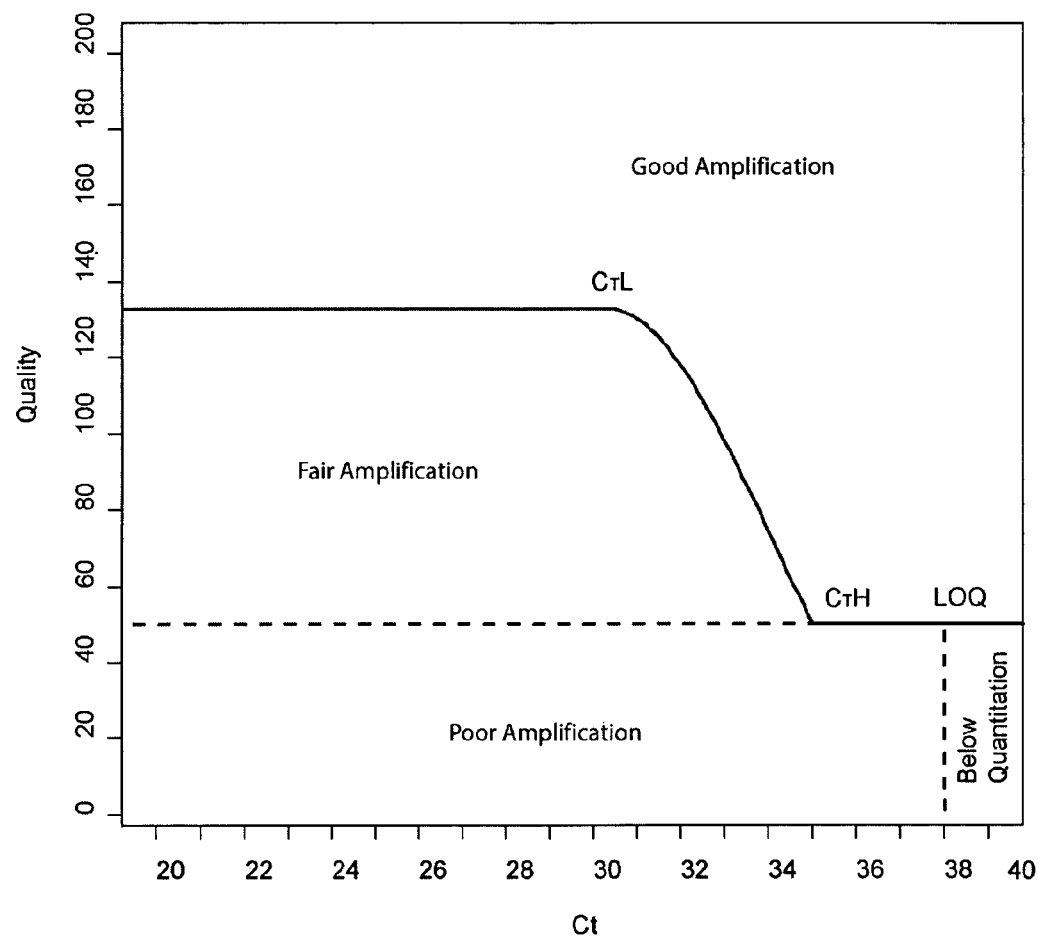

Figure 9: QDAS Status Classification Process
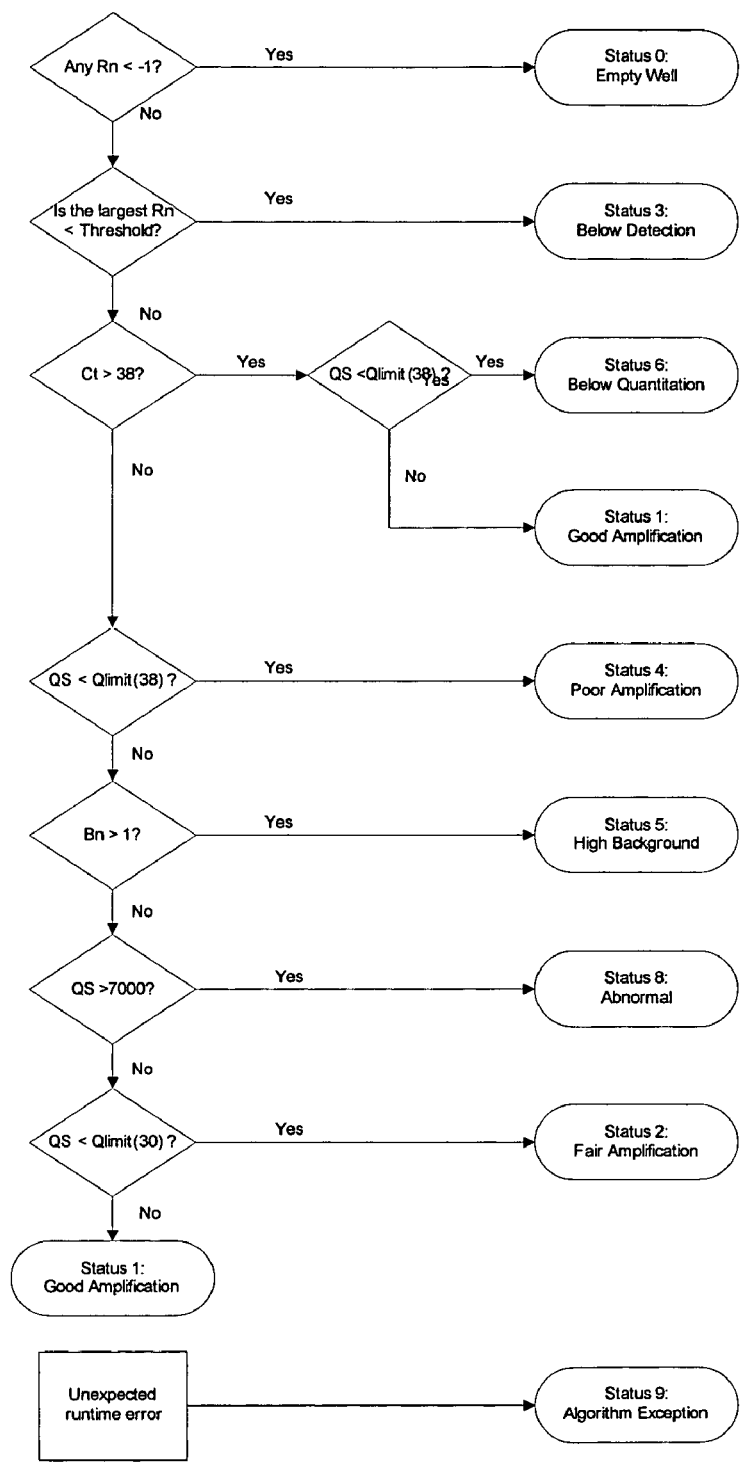

Figure 10: Early Glitch Amplification Example
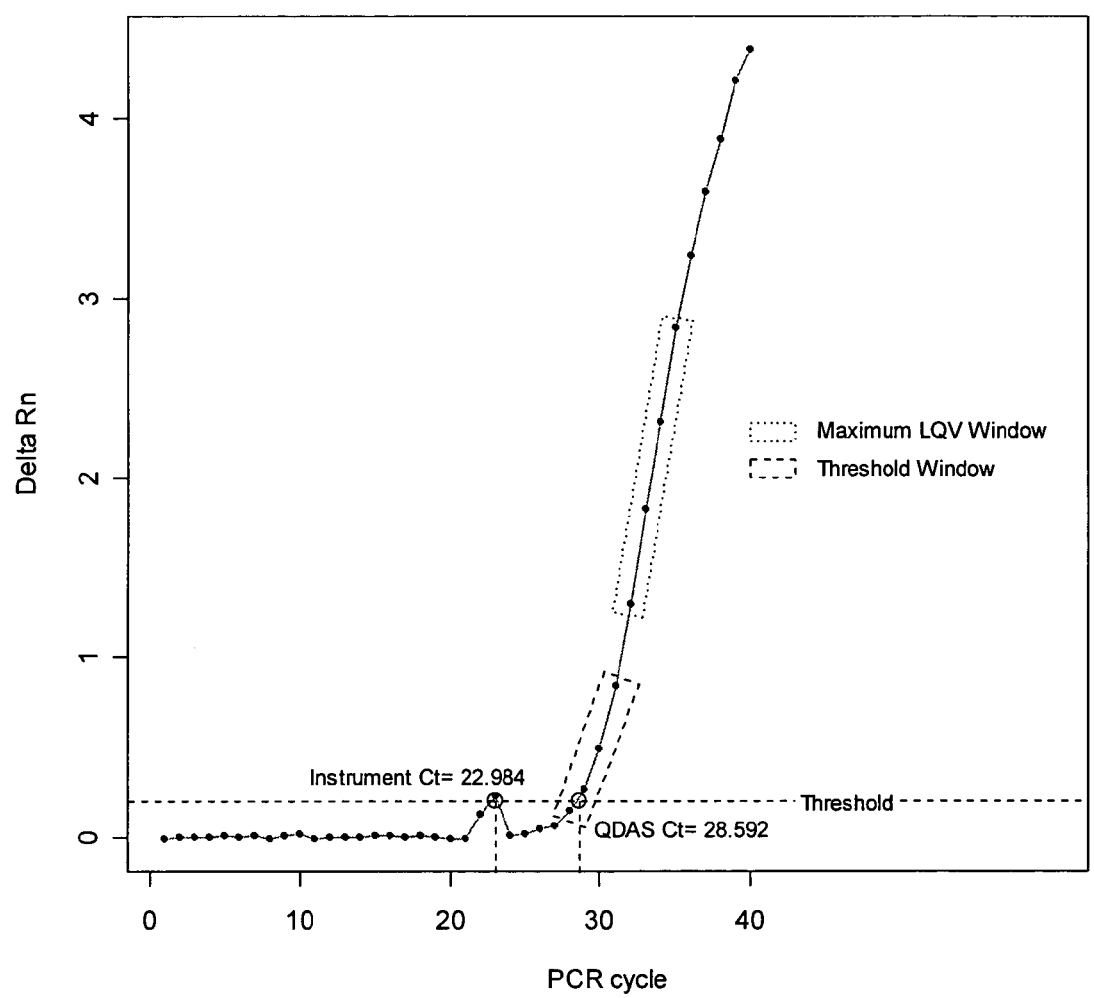

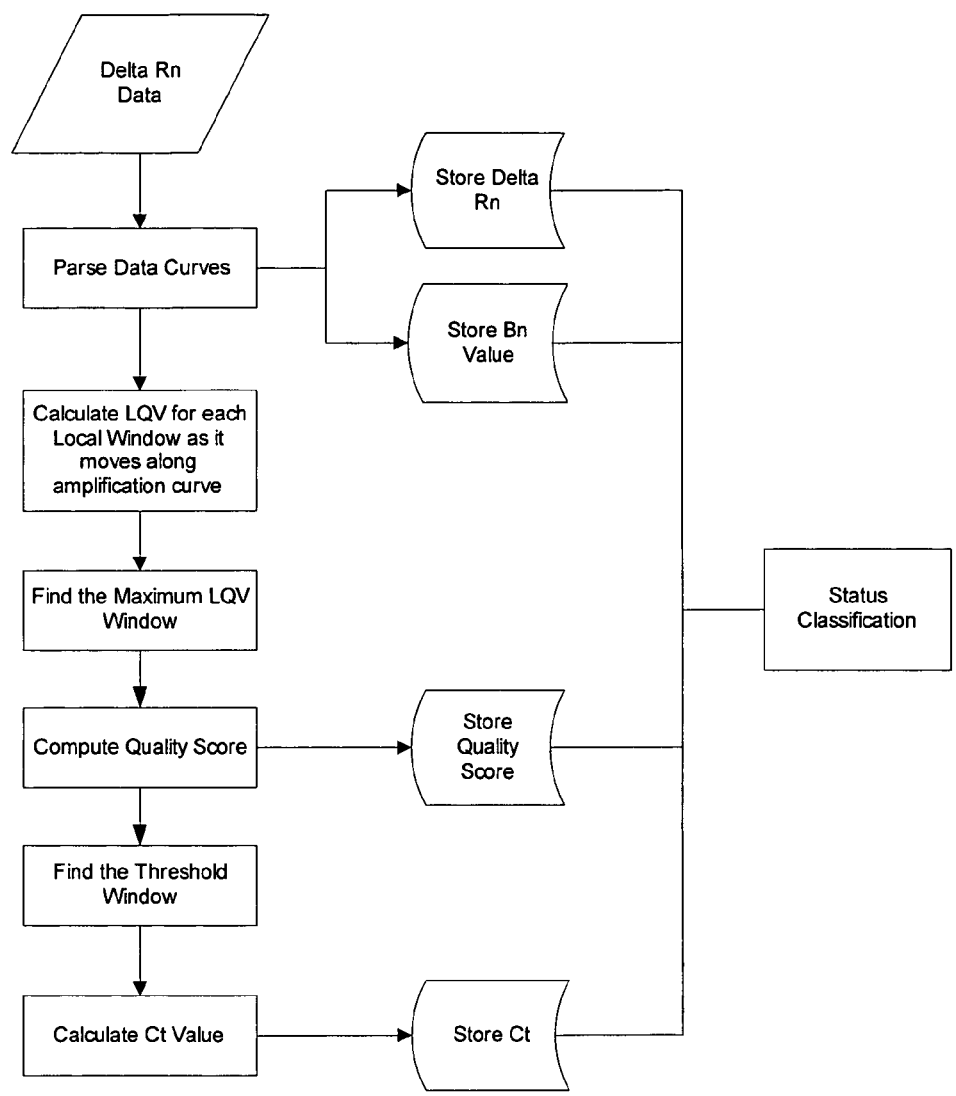
Figure 11: QDAS Analysis System Process Flow

Figure 12: Rn and Delta Rn Example QPCR Data

| PlateID | WellID | Observation | Rn | DeltaRn |
|---|---|---|---|---|
| 163 | 1 | 1 | 0.91859126 | 0.0026579178 |
| 163 | 1 | 2 | 0.9172261 | -0.000609132 |
| 163 | 1 | 3 | 0.92156243 | 0.0018253601 |
| 163 | 1 | 4 | 0.9211552 | -0.00048372382 |
| 163 | 1 | 5 | 0.9264369 | 0.002896098 |
| 163 | 1 | 6 | 0.923738 | -0.0017046654 |
| 163 | 1 | 7 | 0.9214869 | -0.005857619 |
| 163 | 1 | 8 | 0.9245152 | -0.0047312104 |
| 163 | 1 | 9 | 0.9367116 | 0.005563346 |
| 163 | 1 | 10 | 0.9338107 | 0.00076058274 |
| 163 | 1 | 11 | 0.94042563 | 0.005473641 |
| 163 | 1 | 12 | 0.93537456 | -0.0014792406 |
| 163 | 1 | 13 | 0.9360021 | -0.002753588 |
| 163 | 1 | 14 | 0.9413028 | 0.00064524775 |
| 163 | 1 | 15 | 0.94240516 | -0.00015422935 |
| 163 | 1 | 16 | 0.94939595 | 0.004934696 |
| 163 | 1 | 17 | 0.9434795 | -0.0028836452 |
| 163 | 1 | 18 | 0.95246744 | 0.004202453 |
| 163 | 1 | 19 | 0.95108145 | 0.00091460114 |
| 163 | 1 | 20 | 0.9518359 | -0.00023284787 |
| 163 | 1 | 21 | 0.9530913 | -0.00087926025 |
| 163 | 1 | 22 | 0.9544387 | -0.0014337623 |
| 163 | 1 | 23 | 0.9593108 | 0.001536516 |
| 163 | 1 | 24 | 0.9586108 | -0.0010654056 |
| 163 | 1 | 25 | 0.96768755 | 0.0061095036 |
| 163 | 1 | 26 | 0.96764845 | 0.004168538 |
| 163 | 1 | 27 | 0.96746236 | 0.0020805872 |
| 163 | 1 | 28 | 0.98566866 | 0.018385021 |
| 163 | 1 | 29 | 0.9935662 | 0.024380712 |
| 163 | 1 | 30 | 1.0006329 | 0.029545514 |
| 163 | 1 | 31 | 1.0333288 | 0.060339537 |
| 163 | 1 | 32 | 1.0948122 | 0.11992106 |
| 163 | 1 | 33 | 1.1975564 | 0.22076347 |
| 163 | 1 | 34 | 1.3647963 | 0.3861015 |

Figure 13: Example Relational Database Schema Diagram
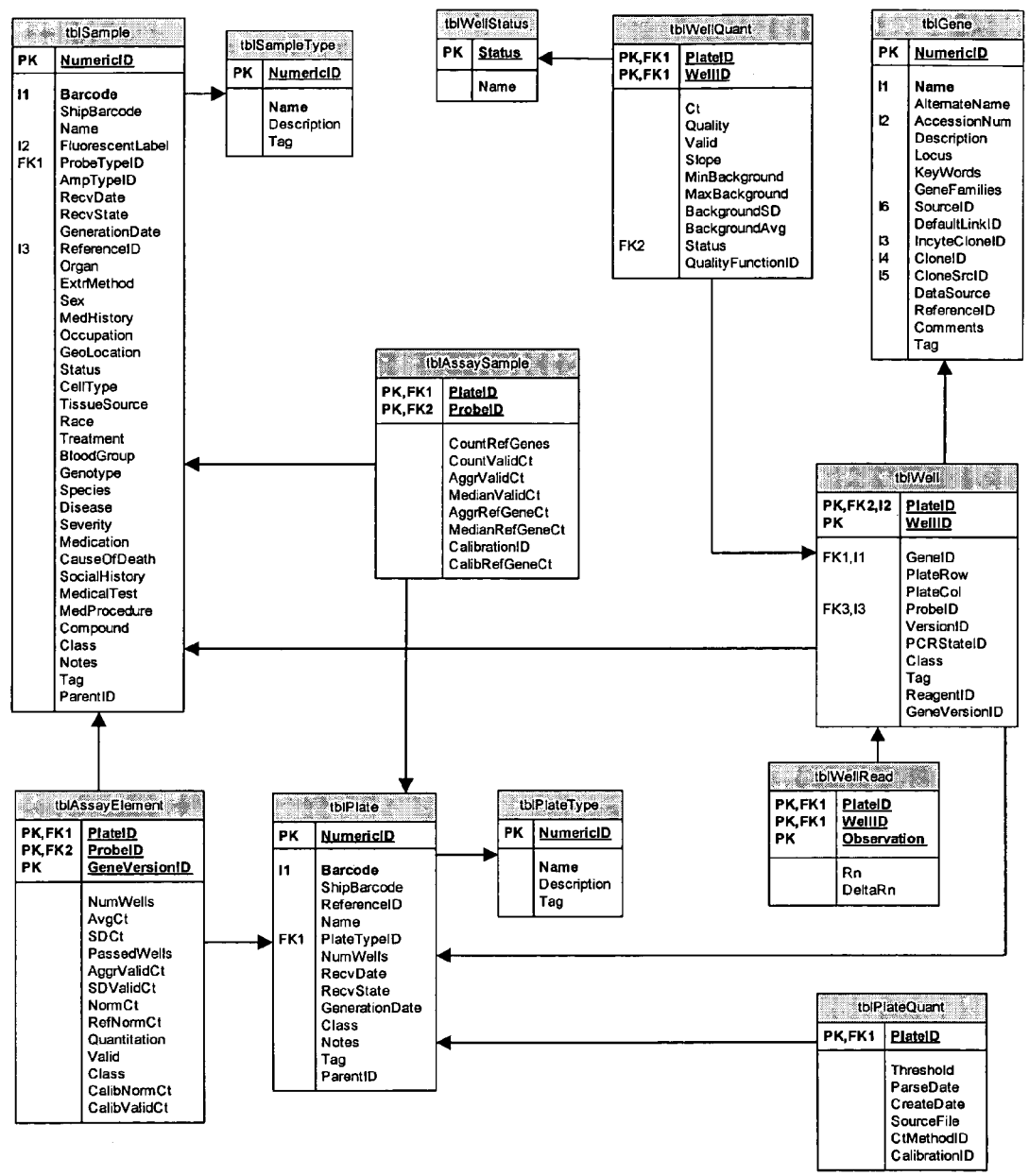

Figure 14: QDAS Data Analysis System
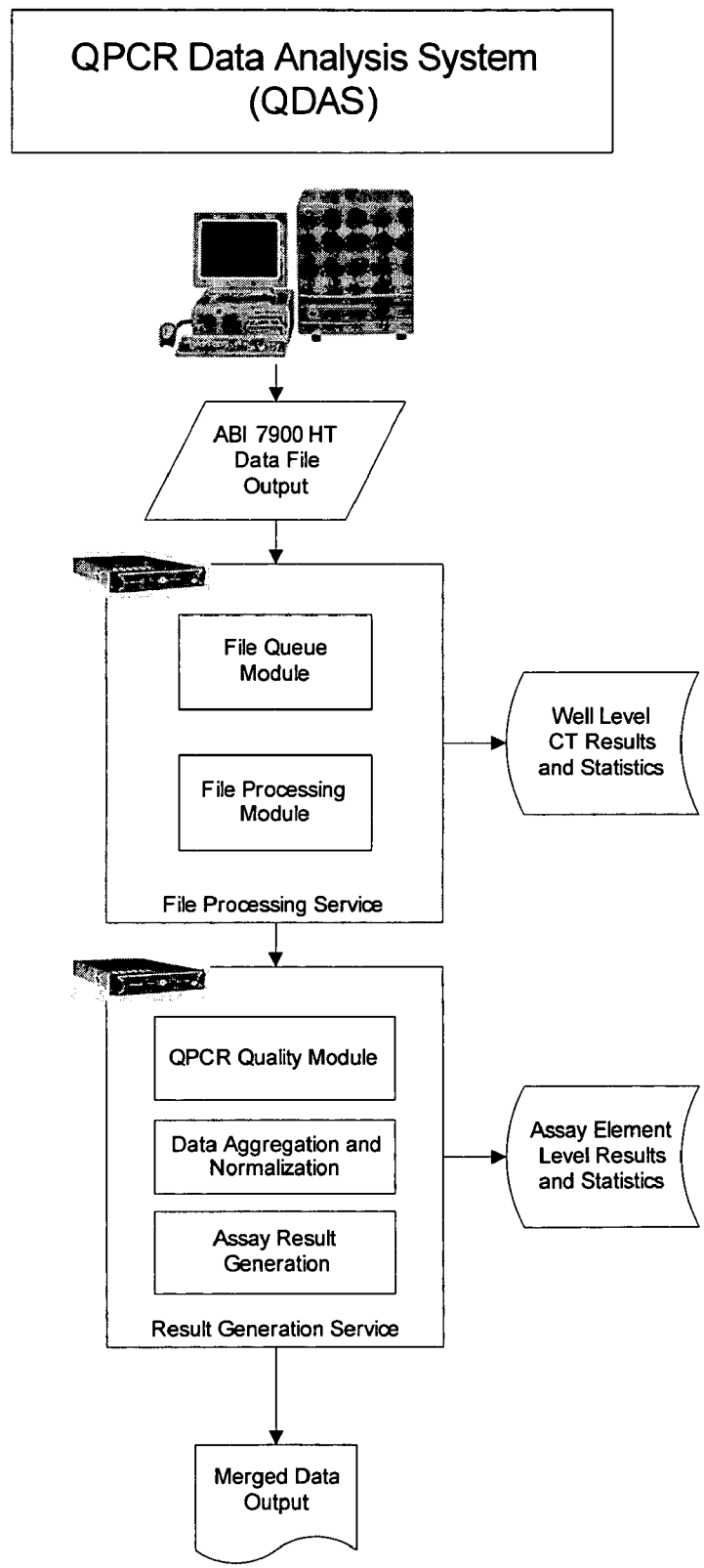

Figure 15 QDAS Processors
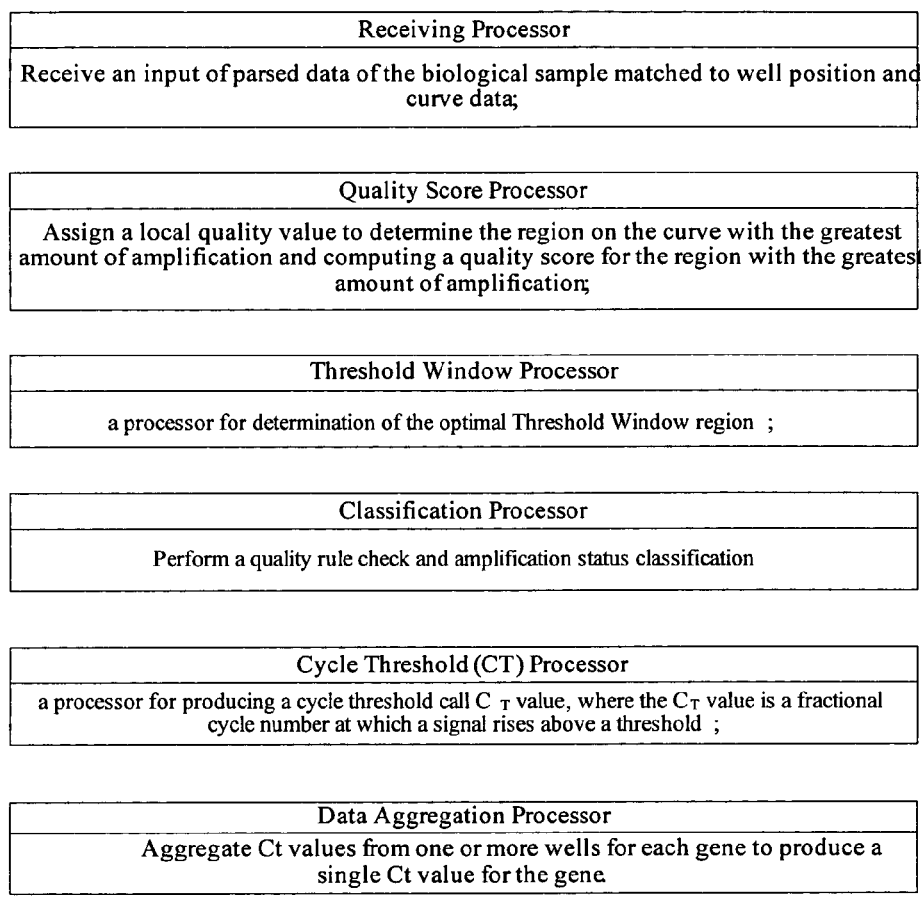

METHOD FOR QUANTITATIVE PCR DATA ANALYSIS SYSTEM (QDAS)

BACKGROUND OF THE INVENTION

1. Field of the Invention

This invention relates generally to methods that improve the accuracy of gene expression profiling, and more particularly to methods for quantitative PCR (QPCR) used to determine the level of gene expression or gene copy number in a high-throughput fashion.

2. Description of the Related Art

The ability to monitor the real-time progress of the Polymerase Chain Reaction (PCR) has revolutionized the way one approaches quantification of DNA and RNA. A real-time quantitative PCR (QPCR) assay provides a large dynamic range of detection and a highly sensitive method for determining the amount of DNA template of interest. When QPCR follows a reverse transcription reaction, it can be used to quantify RNA templates as well. QPCR makes quantification of DNA and RNA much more precise and reproducible because it relies on the analysis of PCR kinetics rather than endpoint measurements.

The determination of DNA or RNA levels of biological samples in a high throughput fashion has been made possible by the QPCR instrument. Commercially available QPCR instruments, and related data acquisition and analysis software, process QPCR assay data generated from biological samples. These systems report quantitative results by calculating a threshold cycle ($C_T$) value as the fractional PCR cycle number where the reporter signal rises above a threshold set manually by a human or automatically by software. The precision and reproducibility of the quantitative result for gene expression depends on the accuracy of this $C_T$ value.

FIG. 1 illustrates a typical 40 cycle amplification graph generated by a QPCR analysis system. When the data is displayed in a logarithmic plot of reporter signal vs. cycle number (FIG. 2), a typical amplification curve manifests four distinct phases that characterize the progression of the PCR reaction. These four phases can be termed as Initial Phase, Geometric Phase, Linear Phase, and Plateau Phase.

The initial phase is characterized by a low level amplification signal within the background noise of the assay. The initial phase begins at the first cycle and ends prior to the beginning of the geometric phase.

The geometric phase is characterized by high and constant amplification efficiency. It may also be referred to as the exponential amplification phase, or log phase. The geometric phase begins at the first detectable rise in reporter signal above background and ends prior to the beginning of the linear phase. When plotted on a log scale of signal vs. cycle number, the curve generated by the geometric phase should approximate a straight line with a slope. A commercial QPCR instrument typically delivers sufficient sensitivity to detect at least 3 cycles in the geometric phase, assuming reasonably optimized PCR conditions.

The linear phase is characterized by a leveling effect where the slope of the amplification curve decreases steadily. At this point, one or more reaction components have fallen below a critical concentration and the amplification efficiency has begun to decrease. This phase is termed linear, because amplification approximates an arithmetic progression, rather than a geometric increase.

Finally, the amplification curve achieves the plateau phase at which time the PCR amplification levels and the reporter signal remains relatively constant.

QPCR instrumentation software is designed to monitor, record, and analyze the real time fluorescent signal data through these phases and then calculate a $C_T$ value that can be used to estimate the initial quantity of the DNA templates. Detection of the geometric phase is the key to high-precision $C_T$ values and reliable QPCR results. At any given cycle or fractional cycle within the geometric phase the amount of product in theory is proportional to the initial number of template copies.

In a high throughput environment, an erroneous $C_T$ value may be reported by software due to several factors including data variation, inefficient amplification, non-specific amplification, and background noise. Such estimation errors may lead to invalid or incomparable assay results.

The limitations of currently available commercial software that may lead to an erroneous quantitation result include the following:

The automatic or manual setting of a threshold for each assay plate may not be appropriate. In order to compare the gene expression levels with accuracy across different patient samples or different genes, the threshold may need to be set as a fixed value in the geometric phase region.

A false $C_T$ value due to atypical or low efficiency amplification. For example, a $C_T$ value generated an the amplification with a linear rise in the fluorescent signal due to non-specific amplification or probe degradation.

A false reported Ct value due to a PCR cycle "glitch" or instrument measurement error. For example, a non-homogenous reaction condition or transient fluorescent reading can cause the fluorescent signal to rise above threshold as shown in FIG. 10.

An inaccurate reported $C_T$ value due to reference signal changes. For example, a decrease in a reference signal, such as ROX, or high variability of background fluorescence may distort the amplification curve and generate an inaccurate $C_T$.

Software algorithms and products that have been surveyed can perform computations in ideal amplification situations but may perform less reliably or generate inaccurate results when an amplification is marginal or poor. In general, they do not have mechanisms to detect errors automatically, and require the user to manually flag or reject invalid results.

There is a need for improved methods and system to analyze and quantify QPCR results. There is a further need to quantify QCPR results to achieve reliable and statistically significant results to profile expression of genes of diagnostic and prognostic importance. There is a further need for automated methods and systems for the quality control and accurate computational analysis of QPCR data. There is yet a further need for improved methods and system to profile the expression of genes with a reduced error rate in a high throughput setting.

SUMMARY OF THE INVENTION

Accordingly, an object of the present invention is to provide improved methods to quantify QPCR results.

Another object of the present invention is to provide improved methods to profile the expression of genes of diagnostic and prognostic importance.

Another object of the present invention is to provide improved methods to profile the expression of genes of diagnostic and prognostic importance with reduced errors and improved quality in a high-throughput setting.

Yet another object of the present invention is to provide methods for the implementation of an automatic computer program.

These and other objects of the present invention are provided in a method of measuring data. In this method, data values are extracted from an assay to generate a data curve. The amplification quality and variability characteristics of the data curve are estimated. A Quality Score (QS) is determined for the amplification curve. An optimal region for threshold cycle ($C_T$) computation is identified and a $C_T$ value is calculated. An overall status classification is made of the amplification curve.

In another embodiment of the present invention, an automated method is provided for processing gene expression information generated from a biological sample. A set of input data generated from the biological sample, gene information, and assay layout specification are received. A Quality Score (QS) is computed for the region with maximum Local Quality Value (LQV). A status classification is made based on the quality score. A threshold cycle ($C_T$) value is estimated for the threshold intersection in closest proximity to the region of maximum LQV. The $C_T$ value is reported as the fractional cycle number at which the assay signal rises above a threshold. The $C_T$ result is mapped to sample and gene information. The $C_T$ results are aggregated from one or more wells to produce a single $C_T$ value for each gene.

In another embodiment of the present invention, an automated method is provided for processing gene expression information of a biological sample. The biological sample, reagent information and containers are received. The status and quality information is monitored and processed for the biological sample, reagents and containers. An output of fluorescence data representative of a gene expression is generated for each biological sample. The fluorescence data is parsed and stored in a database. An input of parsed fluorescence data is received and is data matched by well position and cycle number to produce a fluorescence curve. A Local Quality Value (LQV) is calculated for each consecutive and overlapping region on the curve. A Quality Score (QS) is computed for the region with maximum LQV of all the regions. A $C_T$ value is computed for the curve. The data is matched by well position to sample, gene, and reagent information and the results are stored in the database.

BRIEF DESCRIPTION OF THE FIGURES

FIG. 1 illustrates a typical QPCR amplification and phases plotted on a linear scale.

FIG. 2 illustrates a typical QPCR amplification and phases plotted on a logarithmic scale.

FIG. 3 illustrates a maximum LQV window and the threshold window defined by QDAS, where an inset graphic shows the quadratic regression curve and the QDAS $C_T$ calculation.

FIG. 4 illustrates a window shifting method to calculate LQV for each local window.

FIG. 5 is a flowchart for computing Quality Score (QS) and Maximum LQV Window (MLW).

FIG. 6 is a flowchart for determining the QDAS Threshold Window (TW).

FIG. 7 illustrates the background range distribution versus $C_T$ from a study.

FIG. 8 illustrates a quality lower limit function based classification curve.

FIG. 9 illustrates an example of the QDAS status classification process flow.

FIG. 10 illustrates an example of an amplification curve, with commercially available software, that generated an inaccurate Ct value compared to the QDAS resources of the present invention that is able to calculate a correct Ct value.

FIG. 11 illustrates one embodiment of a process flow for QDAS of the present invention.

FIG. 12 illustrates a dataset table of the present invention used to store Rn and Delta Rn data along with some plate and well information.

FIG. 13 illustrates one embodiment of a schema diagram for an RDBMS for QDAS data.

FIG. 14 illustrates one embodiment of a schematic diagram of a QDAS processing system.

FIG. 15 illustrates processors in one embodiment of a QDAS System

DETAILED DESCRIPTION OF THE INVENTION

For purposes of this specification, the following definitions apply:

"Quantitative PCR" or "QPCR" is defined as a polymerase chain reaction (PCR) process which monitors the kinetics of PCR for the quantification of DNA templates. When QPCR follows a reverse transcription reaction, it can be used for the quantification of RNA templates as well.

"Threshold cycle" or "$C_T$" is defined as a fractional cycle number at which a reporter signal rises above a threshold value.

"Threshold" or "threshold value" is defined as the reporter signal value that is used for calculation of threshold cycle ($C_T$).

"Local window" or "LW" is defined as a subsection of the amplification curve with a certain number of data points. The QDAS algorithm characterizes the PCR amplification by using data from each local subsection to approximate the global features of the curve.

"Local quality value" or "LQV" is a measurement that characterizes the trend for the data-points in the "local window" LW. For example, trend might incorporate the slope and the tightness of the data-points in the window region.

"Quality score" or "QS" is defined the "local quality value" LQV of the "maximum local quality window" MLW. It is used as an indicator for characterization of the amplification curve and QDAS classification for the amplification status report.

"Maximum local quality value window", or "maximum LQV window", or "MLW" is defined as the local window with the highest LQV score among all the possible local windows for a given amplification curve. The LQV score for the MLW is defined as the quality score for the whole amplification.

"Threshold window" or "TW" is defined as the local window that is closest to MLW and across threshold value by a defined margin.

"Reporter normalized" or "Rn" is defined as the reporter signal normalized (divided) by a passive reference signal.

"Subtracted reporter normalized" or "Delta Rn" is defined as the reporter signal subtracted the background and then normalized by the passive reference signal.

"Passive reference signal" is defined as the signal generated by a stable reagent added into the sample reaction. It is used to monitor reaction volume difference.

"Reporter signal" is defined as the signal generated by a PCR product reporter. It is used to measure the amount of PCR product. It is defined as a more general term in this document, and could be referenced more specifically as reporter normalized (Rn), or subtracted reporter normalized (Delta Rn).

"Quantitative PCR analysis system", or "QPCR analysis system", or "QDAS" is defined as the implementation of the algorithm and system depicted in this documentation.

"QDAS $C_T$" or "$qC_T$" is defined as the $C_T$ value calculated by the QDAS algorithm. The $qC_T$ concords with the $C_T$ values calculated by commercial instrumentation software, but reports more accurate and consistent Ct values when data is less than ideal.

"Background normalized" or "Bn" is defined as the difference between the reporter normalized (Rn) and the subtracted reporter normalized (Delta Rn). It is the absolute background and noise measured by QPCR instrument, normalized (divided) by the passive reference signal.

In one embodiment of the present invention, methods and systems are provided for measuring biological data, including but not limited to data for cycling reactions. Examples of suitable data include but are not limited to, fluorescent signal data, optical signal data, magnetic signal data, and electronic signal data. Any number of assays are suitable, including quantification of DNA by QPCR and quantification of RNA by RT-PCR. The shape and characteristics are estimated of an amplification curve. A Quality Score (QS) is produced for a region of maximum LQV for the amplification curve. A $C_T$ value is calculated as illustrated in FIG. 3. A status classification is made of the amplification curve. The status classification can be any one of a set of classifications enumerated in Table 1.

In one embodiment, automated methods and systems are provided for measuring the quality of a QPCR amplification curve and performing localized curve fitting. This embodiment includes the following steps:

a data processing service extracts the data from the QPCR assay.

a windowing method is used to estimate the shape and characteristics of the amplification curve;

a Local Window (LW) is used to characterize the local features for a section of amplification curve.

a Local Quality Value (LQV) is computed based on the slope (1st derivative) and correlation coefficient (R) of the amplification curve by localized linear regression within each window;

a window region with maximum LQV is identified.

a Threshold Window (TW) is identified as the window that intersects the threshold and is closest to the maximum LQV a $C_T$ is calculated based on localized quadratic regression on the Threshold Window;

a Quality Score (QS) for the curve is assigned as the maximum LQV of all window regions.

a status classification is made, as illustrated in FIG. 4.

In one embodiment, a measurement of LQV is made at each region along an amplification curve. The region with maximum LQV is indicative of the effectiveness of the amplification. A Threshold Window is identified and used to calculate a $C_T$ value. The method reduces the occurrence of false $C_T$ values due to high variation of data. An amplification curve may intersect the threshold multiple points. Our definition of the Threshold Window will select the optimal intersection as illustrated in FIG. 5.

In one embodiment, a reporter signal is generated by the fluorescent signal of a chemical reagent. A passive reference signal is generated by the fluorescent signal of a second chemical reagent. At the conclusion of a PCR assay run, a reporter file is generated. The reporter file contains Rn and Delta Rn values of each PCR cycle for the each plate well, and serves as the input file for QPCR DATA ANALYSIS SYSTEM (QDAS). The QDAS system performs data quantification and quality determination. By way of illustration, and without limitation, 40 Rn values and 40 Delta Rn values are read by the QDAS. The Rn and Delta Rn values are stored in a database. In one embodiment, the values are stored in a relational database schema and dataset table as illustrated in FIG. 6.

Data modeling procedures typically try to find a global mathematical function for the representation of data curves. However, these methods are not always practical due to the wide range of features of amplification curves in real-world situations. In this invention, we utilize a windowing method to perform localized approximation of the assay data curve. Localized approximation allows the system to capture the critical trend as expressed by slope and correlation coefficient for each subsection of the curve and summarize these measurements as a global score that can be used to classify the amplification.

The QDAS performs a curve fit (regression) for each shifting window of the curve. The window is defined as a region along the curve that includes a set of adjacent data points. The shifting window is defined as each overlapping window along the curve (FIG. 5). The window is used to estimate the slope (first derivative) and variation for each window of the curve. The window size can range from 1 data point up to the total number of cycles.

There are two considerations for choosing the number of points for the shifting window. The more data points are included, the more sensitive the model is to the data variation. More data points have a higher risk of rejecting reasonably good amplification curves. The fewer data points included, the less sensitive the model to data variation. Fewer data points have a higher chance of accepting a poor curve and may generate a false high Quality Score. In one embodiment, the window size is optimized to contain four points. A window size of pour points performed reliably on broad range of empirical QPCR datasets.

During a QPCR reaction early PCR cycles tend to have high variation due to the instrument and assay start-up (FIG. 1). To better accommodate this variation, the shifting window can have the options to skip these early PCR cycles. In one embodiment, the shifting window skips the first three PCR cycles and starts at the fourth PCR cycle to exclude the high variation. Starting at the fourth PCR cycle, a window represented by a four-point data frame is generated that consists of the following arrays: 1) a four-element, one-dimension array that stores the four consecutive cycle numbers, and 2) a four-element, one-dimension array that stores the Delta Rn values. In certain embodiments all or a portion of the windows overlap the adjacent data windows. FIG. 4 illustrates one working example of the window shifting method with overlapped windows.

In one embodiment, a linear-least-squares regression is utilized and calculates the slope and correlation coefficient (R). The calculation is repeated for all the possible four point window of consecutive cycles. For each window a Local Quality Value (LQV) is computed. The LQV incorporates the slope measurement and correlation coefficient.

The LQV is calculated according to the following function:

$$LQV = 1000 * \text{Slope} * \frac{2}{\pi} * \arcsin(R)$$

The following three factors are incorporated into the LQV function.

"1000": A scaling factor that will bring the final Quality Score (QS, or maximum LQV) into the range from zero to about 1000.

2). "Slope": The slope of the fitted line on the four-point data frame, which measures the efficiency of PCR. The value ranges from about zero to about 1.0. The value for typical successful PCR reactions ranges from 0.1 to 0.7. Slope is the dominant factor (most weighted) for the Quality Score (QS, or maximum LQV) in comparison to the correlation coefficient (R).

3). "2/pi*arcsin(R)": The correlation coefficient R has the value range from −1 to 1 in theory. It measures the tightness of the four points. However for the four-point window with the maximum LQV, its value mostly ranges from 0.8 to 0.99999 with distribution skewed towards higher value end (close to 1) given reasonable PCR success rate. If the coefficient was directly factored into the LQV, it would have only minimum effect on the Quality Score (QS, or maximum LQV). For this reason, the correlation coefficient (R) is transformed using the arcsin function, which increases the spread on the data. In order to bring the range back to (−1, 1) after the transformation, the coefficient of "2/pi" is introduced. After the transformation, the correlation coefficient (R) will have a noticeable effect on the Quality Score (QS, or maximum LQV) but Slope remains the dominant factor.

The region of maximum slope corresponds to the linear phase of the PCR curve. This region is the four cycle window where amplification is occurring at the most rapid rate.

The final quality for the PCR is determined by the characteristics on the four-point data frame with the maximum LQV. The Quality Score (QS) is based on two parameters: 1) the slope of the fitted line on the four-point data frame, which measures the efficiency of PCR, and 2) the correlation coefficient (R), which measures tightness of the four points.

Quality Score=MAX(Window LQV)

The four-point window with the maximum LQV is used to represent the overall quality of the assay well. This Quality Score (QS) is used to determine the Pass/Fail status of the curve and to determine the cycle threshold.

An automated algorithm, QDAS algorithm, can be utilized in the calculation of an accurate $C_T$ value. In one embodiment, a localized curve fitting strategy is used to determine a precise $C_T$ value. The algorithm is illustrated in FIG. 5 and FIG. 6, and detailed below.

The QDAS algorithm uses the window that intersects the threshold and is closest to the curve region with maximum LQV. This window is named as Threshold Window. Once the maximum LQV has been determined, the QDAS program finds the Threshold Window that intersects the threshold and is closest to the maximum LQV window by shifting the window towards the threshold (FIG. 3, and FIG. 4). In order to tolerate data variation for a good PCR amplification, the window is shifted beyond the desired threshold by a specified margin. An upper threshold and lower threshold is defined as the $C_T$ calling threshold plus or minus the defined margin. In one embodiment, the margin is 10% of the threshold value, such that the resulting lower threshold is 90% of the threshold value and the upper threshold is 110% of the threshold value.

Example values for these thresholds are shown in Table 1.

TABLE 1

An example set of threshold values

|  | $C_T$ Calling Threshold | Lower Threshold | Upper Threshold |
|---|---|---|---|
| Value | 0.20 | 0.18 | 0.22 |

If the smallest Delta Rn value for the maximum LQV window is greater than the lower threshold, the QDAS algorithm will shift backward to a window such that the smallest Delta Rn value is less than the lower threshold. If the largest Delta Rn value for the maximum LQV window is less than the upper threshold, the QDAS algorithm will shift forward to a window such that the largest Delta Rn value is greater than the upper threshold.

Curve fitting is performed on the Threshold Window data to estimate a $C_T$ value. The curve fitting employed can be any reasonable method, including but not limited to, linear least squares regression, quadratic least squares regression, or polynomial regression. The number of data points used for the regression can be any number that is greater than one. In one embodiment, a quadratic least squares regression curve fitting method is used to fit the curve and a window size of four points is used for the regression.

After the quadratic regression curve fitting is performed, the $C_T$ value for the point where the fitted quadratic curve crosses to the $C_T$ calling threshold line will be the projected $C_T$ value. The $C_T$ value thus projected is referred as QDAS $C_T$.

A complication that arises when projecting the QDAS $C_T$ is that mathematically the threshold line will have two crossing points on the fitted quadratic curve. Although typically only one point falls within the threshold window, the algorithm must select the appropriate intersection in all cases. In one embodiment, the QDAS algorithm selects the appropriate intersection as follows:

If only one intersection point falls within the PCR cycle range of the Threshold Window, it will be selected. In most cases, it is the right-most point.

In certain cases that both points are outside the Threshold Window range, the program will pick up the cross point that is closer to the lowest point of the Swing four point window.

In the rare case where there is no intersection point, a linear curve fit is used to estimate the $C_T$ value. However in this case, it typically indicates a high data variation in the Threshold Window that a precise $C_T$ cannot be determined. An "abnormal curve" status is reported as described in table 4.

The parabolic regression algorithm employed is designed to fit the parabolic curve by the least-squares method according to the following function formula:

$$y=ax^2+bx+c$$

where x and y are variables. In this document, y is substituted with the Delta Rn value, and x the PCR cycle number for the regression. Using this formula for the computation of the cycle threshold, $C_T$ is the solution of the equation:

$$\text{threshold}=a(C_T)^2+b(C_T)+c$$

The four-point data-frame of maximum LQV and the calculation of the QDAS $C_T$ value using these methods is illustrated in FIG. 3:

The linear regression algorithm employed when there is no parapolic intersection point and is designed to fit the line by least-squares method according to the following function formula:

$$y=ax+b$$

where x and y are variables. In this document, y is substituted with the Delta Rn value, and x the PCR cycle number for the regression. Using this formula for the computation of the cycle threshold, $C_T$ is the solution of the equation:

$$\text{threshold}=a(C_T)+b$$

The Delta Rn value for a QPCR reaction is composed of signal readings from several chemicals as well as a background signal component. A signal reading can be any quantitative reading acquired by the QPCR instrument, including but not limited to optical reading, magnetic reading, and electric signal reading. The signal readings typically contain a passive reference so all other signals can be normalized by the volume of reaction in each well, and reduce the variance caused by volume variation during sample handling. The Reporter Normalized (Rn) value is derived from a signal reading and normalized against the passive reference.

As we defined the Background Normalized (Bn), the Delta Rn value can be expressed as the difference between the Rn value and normalized background signal as shown in the following formula:

$$\text{Delta}Rn = Rn - Bn$$

The passive reference signal in the PCR reaction may decrease as the cycle number increases. Generally, any decrease in passive reference signal is marginal and its effect is negligible. However, in some cases the decrease in the passive reference signal may be drastic or rapid. When this happens, it will lead to an abnormal increase in normalized background and as well as the Rn value. The resulting amplification curve is therefore distorted or skewed and the projected $C_T$ will be inaccurate.

In order to characterize this kind of background error, we implement a background normalized (Bn) range cutoff value.

As a working example, we analyzed the data from one clinical study (Providence Phase II). FIG. 7 shown below plots the Bn Range versus the QDAS $C_T$ values for all data points (a total of 79156 wells) from this study. For the majority of the samples, the range for the background normalized signal is less than 0.8. When the Bn range was larger than 0.8, it may distort the amplification graph and generate a false $C_T$ value.

If the Bn range is greater than the configured Bn threshold, QDAS will label the sample as "High Background"

Genes with low expression can be handled effectively by the following algorithm, which are provided by way of illustration, and without limitation:

If the Delta Rn value of a well never rises above the threshold, the well status is marked as below detection and the $C_T$ value is reported as 40. If the Delta Rn crosses the threshold at a high $C_T$ (~38 or greater) and the Quality Score is low (<=~50) effectively due to non-specific amplification, the well status is marked as below quantification and the $C_T$ value is reported as 40.

Generally a higher Quality Score indicates a better PCR amplification. A low Quality Score indicates a bad or failed amplification. A Quality Score cutoff value can be used to categorize the amplification results for quality control. The determination of cutoff value will vary depending on the study. The examples of cutoff value include but are not limited to a constant value and a variable value determined by a function.

In one embodiment, a lower limit for quality scores can be selected to categorize the quality of amplification curves using a function. Note that Quality Scores have a $C_T$ dependent component because they are predominantly based on the slope of the QPCR curve. As $C_T$ values increase, the maximum theoretical quality score decreases, so a fixed cutoff is not preferable.

By way of illustration, and without limitation, data from two clinical studies and commercial patient samples were analyzed, an approximate one-sided 95% lower prediction interval was determined, and a cubic function modeled for a set of genes.

In one embodiment, a Quality Lower Limit Function is defined in the form:

$$QLimit(C_T) = \begin{cases} a + b(C_TL) + c(C_TL)^2 + d(C_TL)^3 & \text{when } C_T < C_TL \\ a + b(C_T) + c(C_T)^2 + d(C_T)^3 & \text{when } C_TL \leq C_T \leq C_TH \\ a + b(C_TH) + c(C_TH)^2 + d(C_TH)^3 & \text{when } C_T > C_TH \end{cases}$$

Where a, b, c, d are coefficients for the cubic function modeled.

Where $C_TL$ and $C_TH$ are the lower $C_T$ point and higher $C_T$ point respectively that define sections for well classification based on quality scores.

We have also defined LOQ (limit of quantitation) as the $C_T$ value beyond which quality scores less that the QLimit($C_TH$) are classified as Below Quantitation. In general, Wells with quality scores greater than or equal to QLimit ($C_T$) are classified as Good Amplifications.

Wells with quality scores less than QLimit($C_T$) are classified depending on the $C_T$ values as follows:

For $C_T$ values less than or equal to $C_TH$
Wells with quality score greater than or equal to QLimit($C_TH$) are classified as Fair Amplifications.
Wells with quality score less than QLimit($C_TH$) are classified as Poor Amplifications.

For $C_T$ values greater than $C_TH$, wells are classified as Below Quantitation.

As a working example, the following table shows a set of parameters used to determine the QLimit function. The "default" signifies that the parameter set is used for any gene not explicitly configured.

The graph in FIG. 8 illustrates the use of the Quality Lower Limit Function curve for well classification, using the Default parameter set shown in Table 2.

TABLE 2

QLimit Function parameter table with example values

|  | ID | a | b | C | d | $C_TL$ | $C_TH$ |
|---|---|---|---|---|---|---|---|
| Default | 1 | −7064.9021275 | 630.1587625 | −17.8553345 | 0.1631267 | 30.0 | 38.0 |
| CTSL2 | 2 | −22552.507815 | 2040.021163 | −60.5611297 | 0.59217 | 30.5 | 35.0 |
| CCNB1 | 3 | −886.03847054 | 46.07595073 | 0.181703553 | −0.01967 | 31.5 | 38.0 |

During the geometric phase and linear phase an amplification curve generally rises smoothly as the PCR cycle number increases resulting in a monotonic curve. If the curve for the region between TW and MLW is not monotonic, it is an indication of inaccurate $C_T$ value. The QDAS algorithm performs a slope evaluation for each LW between TW and MLW (including both TW and MLW). If a slope for any LW is less than zero while the amplification curve rises above threshold value, the curve for this region is not monotonic and the amplification is reclassified as Abnormal Curve.

Parameter values for the QDAS algorithm can be adjusted without limitation in order to accommodate different study and stringency requirements. The following table contains a working example set of parameter values.

TABLE 3

Example QDAS Algorithm Parameters

| Parameter | Description | Example Value | Status Affected | Comments |
|---|---|---|---|---|
| Empty Well Threshold | Lowest Delta Rn Cutoff for empty well | −1.0 | 0: Empty | "−1" works very well for the TAQMAN Assay and ABI 7900 instrument. |
| Cycle Threshold | Threshold for $C_T$ calculation | 0.20 | 3: Below Detection | Value of Cycle Threshold is directly related to $C_T$ projection. |
| Threshold Margin | Margin above/below Cycle Threshold | 0.10 | NA | At "10%", swing margin has negligible effect on $C_T$ projection, but greatly increases ability of Parafit algorithm to deal with exceptions. |
| Background Threshold | Maximum allowable background variation | 0.80 | 5: High Background | Modeled based on study data. |
| Abnormal Curve Threshold | Abnormal amplification curve detection. | 7000 | 8: Abnormal Curve | Quality Score above 7000 |
| CT Method ID | Sequential Version Number for Algorithm Changes | 13 | NA | |
| Q Limit Parameters | Coefficients (a, b, c, d) $C_TL$ and the $C_TH$ | Gene assay dependent | 1 Good Amplification 2 Fair Amplification 3 Poor Amplification 4. Below Quantitation | Each gene assay can store a distinct definition of the cubic curve. |

Downstream data analysis and validation can be performed based on the classification of the amplification curve. By way of illustration and without limitation, the final status for each output of the QDAS program is classified as one of the categories shown in Table 4 below and detailed thereafter.

TABLE 4

Example QPCR Status Classifications

| Status | Description |
|---|---|
| 0 | Empty Well |
| 1 | Good Amplification |
| 2 | Fair Amplification |
| 3 | Below Detection |
| 4 | Poor Amplification |
| 5 | High Background |
| 6 | Below Quantification |
| 8 | Abnormal Quality |
| 9 | Algorithm Exception |

Status "0": Empty

Not all wells in a PCR plate may contain samples or reagents. Certain wells remain empty either purposely by experimental design, or due to a sample handling or tracking error. QPCR always generates some signal reading regardless of whether the well is empty or not. However, if the well is empty, there is no passive reference and the minimum Delta Rn are reported as highly-variable numbers, dominantly negative.

A signal significantly less than zero is used to detect empty wells. When the signal is less than the EmptyWell threshold (−1.0) the algorithm will assign "0" for the status of an empty well.

Status "1": Good Amplification

If the quality score calculated is greater than the lower limit quality function value for the reported $C_T$ it will be assigned a Status "1", "Good Amplification".

Quality>$Q$Limit($C_T$)

Status "2": Fair Amplification

If the quality score calculated is greater than the minimum quality function value for the reported $C_T$ but less than or equal to the lower limit quality function. These wells will be assigned a Status of "2", "Fair Amplification"

$Q$Limit($C_TH$)<Quality<=$Q$Limit($C_T$)

Status "3": Below Detection

If the well is not empty, and the Delta Rn value never rises above threshold value, it will be assigned a Status "3", which means PCR amplification is "Below detection".

all Delta Rn<Cycle Threshold

Status "4": Poor Amplification

If the Delta Rn value rises above threshold value and the quality score calculated is less than or equal to the value of the minimum quality threshold function.

Quality<=QLimit($C_TH$)

Status "5": High Background

If 1) the well is not empty, and 2) the normalized background range is greater than Background Range cutoff value, it will be assigned a Status "5", which means PCR amplification is "High Background". In the current version of the algorithm, the cutoff value is set as "0.8".

Background Range>Background Threshold

Status "6": Below Quantification

High $C_T$ Values (>~38) with extremely low quality (<=~50) are reported as a $C_T$ of 40.

Status "8": Abnormal Curve

This status is reported when an irregular amplification curve is detected. The following conditions will return an "Abnormal Curve" status "8".

If the quality score calculated is more than 7000 and the well is not empty (as defined above. This happens when the QPCR probe dissociates from template or cannot be quenched as PCR proceeds.

If the curve stagnates at threshold. In rare cases, the parabolic fitted curve will not cross threshold because the entire curve at the threshold region is above or below the threshold. For example, in some samples, when the amplification rises close to the threshold, it stagnates and does not increase for three or more cycles in the threshold region. When this happens, the amplification curve is distorted and an accurate $C_T$ cannot be projected. Note in this case a linear curve-fit is used to estimate a $C_T$ but the curve is reported as abnormal.

If a $C_T$ value is reported within the Baseline Normalization region. If $C_T$ value is less than or equal to 15 ($C_T$<=15) then the well is reported as abnormal curve. Values within the baseline region are typically due to high data variation and are not reliable.

If a slope for any local window between the TW and MLW including TW and MLW is less than zero while the amplification curve rises above threshold value, the curve for this region is not monotonic. The Ct value is inaccurate in this case and the amplification will be reported as abnormal.

Status "9": Algorithm Failure

If a computation exception occurs status 9 "Algorithm Failure" is reported.

If a well meets the criteria for multiple status codes, the evaluation order of classification and reporting can be determined based on biological, commercial, or computational factors. By way of illustration, the following is an example evaluation sequence ordering: Empty Well; Below Detection; Below Quantification; Poor Amplification; High Background; Abnormal Quality; Fair Amplification; Good Amplification.

FIG. 9 shows an illustration of a working example of the process flow for the amplification status classification.

As an illustration of the implementation, the following functions have been coded into a working C# program as documented in Table 5.

TABLE 5

A work example set of functions implemented in C# program

| Function | Description |
| --- | --- |
| Regression( ) | The Regression Function does regression on two numerical vectors (arrays) and outputs slope, intercept and correlation coefficient. |
| ProjectCt( ) | The ProjectCt Function calculates a projected $C_T$ values according to a specific threshold setting. |
| CalculateQuality( ) | The CalculateQuality Function calculates a quality score for each PCR amplification curve. |
| CallStatus( ) | The CallStatus Function generates a status call for each PCR amplification based on the quality score and the quality lower limit function. |
| ParaFit( ) | The Parafit Function does regression on two numerical vectors (arrays) and outputs three parabolic coefficients for the fitted parabolic curve. |
| Save( ) | The Save Function updates the WellQuant database table and records the version of the algorithm. At the plate level an external Save function updates information about the plate and algorithm method |

The QDAS programs assume the integrity of the Rn and Delta Rn values from the report file generated by QPCR instrument software. If the QPCR instrument software generates inaccurate measurements or has missing data, for example, due to gross equipment error, the results of the automated QDAS program need to be examined accordingly.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

The invention claimed is:

1. A method of determining a classification of amplification data resulting from an amplification of nucleic acid molecules in a sample, the method comprising:
   receiving, at a computing system, the amplification data, wherein the amplification data is derived from a signal measured from the sample at a plurality of time points, wherein the time points include numbers corresponding to cycles of a reaction of the sample;
   determining, with the computing system, a quality score of the amplification data, wherein the quality score is a maximum of a group of one or more local quality values (LQVs), wherein an LQV is proportional to a slope of a respective window region containing a plurality of the amplification data points;
   determining a fractional cycle number (Ct) where a function approximating at least a portion of the amplification data intersects a Ct threshold value;
   generating, with the computing system, a status classification of the amplification data based on a numerical value of the quality score and based on Ct;
   determining a quality lower limit function (Qlimit) as a function of cycle number, wherein the Qlimit:
      is a first constant value for cycle numbers less than a lower cycle number (CtL);
      decreases from the first constant value to a second constant value, wherein the decrease occurs from CtL to a higher cycle number (CtH); and
      is the second constant value for cycles higher than the CtH value,
   wherein generating the status classification includes identifying a distance between a point of {Ct, quality score} and Qlimit.

2. The method of claim 1, wherein a window region contains a fixed number of amplification data points.

3. The method of claim 2, wherein the fixed number of amplification data points is four.

4. A method of determining a classification of amplification data resulting from an amplification of nucleic acid molecules in a sample, the method comprising:
  receiving, at a computing system, the amplification data, wherein the amplification data is derived from a signal measured from the sample at a plurality of time points, wherein the time points include numbers corresponding to cycles of a reaction of the sample;
  determining, with the computing system, a quality score of the amplification data, wherein the quality score is a maximum of a group of one or more local quality values (LQVs), wherein an LQV is proportional to a slope of a respective window region containing a plurality of the amplification data points;
  determining a fractional cycle number (Ct) where a function approximating at least a portion of the amplification data intersects a Ct threshold value, wherein determining Ct includes:
    determining a threshold window, including:
      when a tolerance threshold value does not lie in the window region with the maximum LQV, moving the window region with the maximum LQV until the window region contains an amplification data point on the other side of the tolerance threshold value;
    calculating the function approximating at least a portion of the amplification data by fitting the function to the amplification data points of the threshold window; and
    determining where the function crosses the Ct threshold value; and
  generating, with the computing system, a status classification of the amplification data based on a numerical value of the quality score and based on Ct.

5. The method of claim 4, wherein determining a threshold window further includes:
  when the tolerance threshold value does lie in the window region with the maximum LQV, using the window region with the maximum LQV as the threshold window.

6. The method of claim 4, wherein if a slope for any window region from the threshold window to the window region with maximum LQV is less than zero while the amplification data rises above Ct threshold value, the status classification is generated as indicating that the amplification data is not normal.

7. The method of claim 4, wherein the tolerance threshold value is equal to the Ct threshold value.

8. The method of claim 4, wherein when the lowest value of an amplification data point in the window region with the maximum LQV is greater than the tolerance threshold value, the window region is moved to lower cycle numbers until the lowest value is less than the tolerance threshold value.

9. The method of claim 8, wherein the tolerance threshold value is 90% of the Ct threshold value.

10. The method of claim 4, wherein when the highest value of an amplification data point in the window region with the maximum LQV is lower than the tolerance threshold value, the window region is moved to higher cycle numbers until the highest value is greater than the tolerance threshold value.

11. The method of claim 10, wherein the tolerance threshold value is 110% of the Ct threshold value.

12. The method of claim 1, wherein generating the status classification further includes:
  generating a first classification when the quality score is higher than Qlimit at Ct; and
  generating at least one other classification when the quality score is lower than Qlimit at Ct.

13. The method of claim 12, wherein the at least one other classification includes:
  a second classification when the quality score is higher than the second constant value;
  a third classification when the quality score is less than the second constant value and the Ct value is below a cycle limit; and
  a fourth classification when the quality score is less than the second constant value and the Ct value is higher than the cycle limit.

14. The method of claim 13, wherein the cycle limit is CtH.

15. The method of claim 13, wherein the first classification is "good amplification", the second classification is "fair amplification", the third classification is "poor amplification", and the fourth classification is "below quantitation."

16. The method of claim 1, further comprising calculating the slope of each respective window region by:
  determining a linear fit to the plurality of the amplification data points in the respective window region; and
  taking the slope of the line as the slope of the respective window region.

17. The method of claim 16, wherein at least a portion of each window region overlaps another window region.

18. The method of claim 17, wherein in each pair of successive window regions, a first window region has one amplification data point not in the second window region, and the second window region has one amplification data point not in the first window region.

19. The method of claim 16, wherein an LQV is also proportional to a correlation coefficient R that measures a tightness of the plurality of the amplification data points in a respective window region relative to the linear fit.

20. The method of claim 19, wherein an LQV is:
$1000*slope*2/\pi*\arcsin(R)$.

21. The method of claim 1, wherein the amplification is a PCR amplification.

22. The method of claim 1, wherein each cycle is a PCR cycle.

23. The method of claim 1, wherein the signal is a fluorescent signal.

24. The method of claim 1, wherein the sample is a QPCR assay.

25. The method of claim 1, wherein a value of the signal is normalized by a volume of the sample as part of deriving the amplification data points.

26. The method of claim 25, wherein the normalization is determined from a passive reference signal generated by a chemical reagent in the sample.

27. The method of claim 25, wherein a background signal is subtracted from the measured signal as part of deriving the amplification data points.

28. A method of determining a Ct value for amplification data resulting from an amplification of molecules in a sample, the method comprising:
  receiving, at a computing system, the amplification data, wherein the amplification data is derived from a signal measured from the sample at a plurality of time points;
  determining, with the computing system, a quality score of the amplification data, wherein the quality score is a maximum of a group of one or more local quality values (LQVs), wherein an LQV is proportional to a slope of a respective window region containing a plurality of the amplification data points;

determining, with the computing system, a threshold window, including:
when a tolerance threshold value does not lie in the window region with the maximum LQV, moving the window region with the maximum LQV until the window region contains an amplification data point on the other side of the tolerance threshold value;

fitting, with the computing system, a function to the amplification data points of the threshold window; and determining, with the computing system, the Ct value as a fractional time point where the function crosses a Ct threshold value.

29. The method of claim 28, wherein the time points include numbers corresponding to cycles of a reaction of the sample.

30. The method of claim 28, wherein the tolerance threshold value is equal to the Ct threshold value.

31. The method of claim 28, wherein when the lowest value of an amplification data point in the window region with the maximum LQV is greater than the tolerance threshold value, the window region is moved to lower cycle numbers until the lowest value is less than the tolerance threshold value.

32. The method of claim 31, wherein the tolerance threshold value is 90% of the Ct threshold value.

33. The method of claim 28, wherein when the highest value of an amplification data point in the window region with the maximum LQV is lower than the tolerance threshold value, the window region is moved to higher cycle numbers until the highest value is greater than the tolerance threshold value.

34. The method of claim 33, wherein the tolerance threshold value is 110% of the Ct threshold value.

35. The method of claim 28, wherein a window region contains a fixed number of amplification data points.

36. The method of claim 35, wherein the fixed number of amplification data points is four.

37. The method of claim 28, further comprising calculating the slope of each respective window region by:
determining a linear fit to the plurality of the amplification data points in the respective window region; and
taking the slope of the line as the slope of the respective window region.

38. The method of claim 37, wherein at least a portion of each window region overlaps another window region.

39. The method of claim 38, wherein in each pair of successive window regions, a first window region has one amplification data point not in the second window region, and the second window region has one amplification data point not in the first window region.

40. The method of claim 37, wherein an LQV is also proportional to a correlation coefficient R that measures a tightness of the plurality of the amplification data points in a respective window region relative to the linear fit.

41. The method of claim 40, wherein an LQV is:
$1000*slope*2/\pi*arcsin(R)$.

42. The method of claim 28, wherein determining a threshold window further includes:
when the tolerance threshold value does lie in the window region with the maximum LQV, using the window region with the maximum LQV as the threshold window.

43. A system for determining a classification of amplification data resulting from an amplification of nucleic acid molecules in a sample, wherein the amplification data is derived from a signal measured from the sample at a plurality of time points, wherein the time points include numbers corresponding to cycles of a reaction of the sample, the system comprising:

a database storing a quality score of the amplification data, wherein the quality score is a maximum of a group of one or more local quality values (LQVs), wherein an LQV is proportional to a slope of a respective window region containing a plurality of the amplification data points; and one or more processors that are communicably coupled with the database and that are programmed to:
determine a fractional cycle number (Ct) where a function approximating at least a portion of the amplification data intersects a Ct threshold value;
determine a quality lower limit function (Qlimit) as a function of cycle number, wherein the Qlimit:
is a first constant value for cycle numbers less than a lower cycle number (CtL);
decreases from the first constant value to a second constant value, wherein the decrease occurs from CtL to a higher cycle number (CtH); and
is the second constant value for cycles higher than the CtH value; and
generate a status classification of the amplification data based on a numerical value of the quality score and based on Ct, wherein generating the status classification includes identifying a distance between a point of {Ct, quality score} and Qlimit.

44. The system of claim 43, further comprising:
a computer output device for displaying the status classification.

45. The system of claim 43, wherein a window region contains a fixed number of amplification data points.

46. The system of claim 45, wherein the fixed number of amplification data points is four.

47. A system for determining a classification of amplification data resulting from an amplification of nucleic acid molecules in a sample, wherein the amplification data is derived from a signal measured from the sample at a plurality of time points, wherein the time points include numbers corresponding to cycles of a reaction of the sample, the system comprising:

a database storing a quality score of the amplification data, wherein the quality score is a maximum of a group of one or more local quality values (LQVs), wherein an LQV is proportional to a slope of a respective window region containing a plurality of the amplification data points; and one or more processors that are communicably coupled with the database and that are programmed to:
determine a fractional cycle number (Ct) where a function approximating at least a portion of the amplification data intersects a Ct threshold value, wherein determining Ct includes:
determining a threshold window, including:
when a tolerance threshold value does not lie in the window region with the maximum LQV, moving the window region with the maximum LQV until the window region contains an amplification data point on the other side of the tolerance threshold value;
calculating the function approximating at least a portion of the amplification data by fitting the function to the amplification data points of the threshold window; and determining where the function crosses the Ct threshold value; and generate a status classification of the amplification data based on a numerical value of the quality score and based on Ct.

48. The system of claim 47, wherein determining a threshold window further includes:
when the tolerance threshold value does lie in the window region with the maximum LQV, using the window region with the maximum LQV as the threshold window.

49. The system of claim 47, wherein if a slope for any window region from the threshold window to the window region with maximum LQV is less than zero while the amplification data rises above Ct threshold value, the status classification is generated as indicating that the amplification data is not normal.

50. The system of claim 47, wherein the tolerance threshold value is equal to the Ct threshold value.

51. The system of claim 47, wherein when the lowest value of an amplification data point in the window region with the maximum LQV is greater than the tolerance threshold value, the window region is moved to lower cycle numbers until the lowest value is less than the tolerance threshold value.

52. The system of claim 47, wherein the tolerance threshold value is 90% of the Ct threshold value.

53. The system of claim 47, wherein when the highest value of an amplification data point in the window region with the maximum LQV is lower than the tolerance threshold value, the window region is moved to higher cycle numbers until the highest value is greater than the tolerance threshold value.

54. The system of claim 53, wherein the tolerance threshold value is 110% of the Ct threshold value.

55. The system of claim 43, wherein generating the status classification further includes:
generating a first classification when the quality score is higher than Qlimit at Ct; and
generating at least one other classification when the quality score is lower than Qlimit at Ct.

56. The system of claim 55, wherein the at least one other classification includes:
a second classification when the quality score is higher than the second constant value;
a third classification when the quality score is less than the second constant value and the Ct value is below a cycle limit; and
a fourth classification when the quality score is less than the second constant value and the Ct value is higher than the cycle limit.

57. The system of claim 56, wherein the cycle limit is CtH.

58. The system of claim 56, wherein the first classification is "good amplification", the second classification is "fair amplification", the third classification is "poor amplification", and the fourth classification is "below quantitation."

59. The system of claim 43, wherein the database stores the amplification data, and wherein the one or more processors are further programmed to calculate the slope of each respective window region by:
determining a linear fit to the plurality of the amplification data points in the respective window region; and
taking the slope of the line as the slope of the respective window region.

60. The system of claim 59, wherein at least a portion of each window region overlaps another window region.

61. The system of claim 60, wherein in each pair of successive window regions, a first window region has one amplification data point not in the second window region, and the second window region has one amplification data point not in the first window region.

62. The system of claim 59, wherein an LQV is also proportional to a correlation coefficient R that measures a tightness of the plurality of the amplification data points in a respective window region relative to the linear fit.

63. The system of claim 62, wherein an LQV is:
$1000 * slope * 2/\pi * \arcsin(R)$.

64. The system of claim 43, wherein the amplification is a PCR amplification.

65. The system of claim 43, wherein each cycle is a PCR cycle.

66. The system of claim 43, wherein the signal is a fluorescent signal.

67. The system of claim 43, wherein the sample is a QPCR assay.

68. The system of claim 43, wherein a value of the signal is normalized by a volume of the sample as part of deriving the amplification data points.

69. The system of claim 68, wherein the normalization is determined from a passive reference signal generated by a chemical reagent in the sample.

70. The system of claim 68, wherein a background signal is subtracted from the measured signal as part of deriving the amplification data points.

71. A system for determining a Ct value for amplification data resulting from an amplification of molecules in a sample, wherein the amplification data is derived from a signal measured from the sample at a plurality of time points, the system comprising:
a database storing the amplification data including data points associated with a quality score that is a maximum of a group of one or more local quality values (LQVs), wherein an LQV is proportional to a slope of a respective window region containing a plurality of the amplification data points; and
one or more processors that are communicably coupled with the database and that are programmed to:
determine a threshold window, including:
when a tolerance threshold value does not lie in the window region with the maximum LQV, moving the window region with the maximum LQV until the window region contains an amplification data point on the other side of the tolerance threshold value;
fit a function to the amplification data points of the threshold window; and
determine the Ct value as a fractional time point where the function crosses a Ct threshold value.

72. The system of claim 71, wherein the time points include numbers corresponding to cycles of a reaction of the sample.

73. The system of claim 71, wherein the tolerance threshold value is equal to the Ct threshold value.

74. The system of claim 71, wherein when the lowest value of an amplification data point in the window region with the maximum LQV is greater than the tolerance threshold value, the window region is moved to lower cycle numbers until the lowest value is less than the tolerance threshold value.

75. The system of claim 71, wherein when the highest value of an amplification data point in the window region with the maximum LQV is lower than the tolerance threshold value, the window region is moved to higher cycle numbers until the highest value is greater than the tolerance threshold value.

76. The system of claim 71, wherein a window region contains a fixed number of amplification data points.

77. The system of claim 71, wherein the one or more processors are further programmed to calculate the slope of each respective window region by:
- determining a linear fit to the plurality of the amplification data points in the respective window region; and
- taking the slope of the line as the slope of the respective window region.

78. The system of claim 71, wherein determining a threshold window further includes:
- when the tolerance threshold value does lie in the window region with the maximum LQV, using the window region with the maximum LQV as the threshold window.

* * * * *